US009965589B2

(12) United States Patent
Williams et al.

(10) Patent No.: US 9,965,589 B2
(45) Date of Patent: May 8, 2018

(54) SYSTEM, APPARATUS FOR USE IN A STERILE FIELD AND METHOD FOR TRACKING, CONFIRMING AND STORING PATIENT AND PROCEDURE INFORMATION USING A UNIQUE DEVICE IDENTIFIER ASSOCIATED WITH A MEDICAL DEVICE

(71) Applicant: S & S Innovations, LLC, Memphis, TN (US)

(72) Inventors: Keith Dawson Williams, Germantown, TN (US); Carlton Dee Evans, Memphis, TN (US)

(73) Assignee: S + S Innovations, LLC, Memphis, TN (US)

( * ) Notice: Subject to any disclaimer, the term of this patent is extended or adjusted under 35 U.S.C. 154(b) by 0 days. days.

(21) Appl. No.: 15/722,267

(22) Filed: Oct. 2, 2017

(65) Prior Publication Data
US 2018/0082027 A1  Mar. 22, 2018

Related U.S. Application Data

(62) Division of application No. 15/315,308, filed as application No. PCT/US2016/033877 on May 24, 2016, now Pat. No. 9,805,162.

(60) Provisional application No. 62/185,638, filed on Jun. 28, 2015.

(51) Int. Cl.
*G06F 19/00* (2018.01)

(52) U.S. Cl.
CPC .......... *G06F 19/322* (2013.01); *G06F 19/325* (2013.01)

(58) Field of Classification Search
None
See application file for complete search history.

(56) References Cited

U.S. PATENT DOCUMENTS

| 5,554,841 A | 9/1996 | Kost et al. |
| 5,631,456 A | 5/1997 | Kost et al. |
| 5,873,814 A | 2/1999 | Adair |
| 8,146,825 B1 * | 4/2012 | Prpa ...................... A61B 90/98 235/470 |
| 8,430,320 B2 | 4/2013 | Prpa |
| 8,651,385 B2 | 2/2014 | Prpa |
| 9,355,289 B2 | 5/2016 | Prpa |
| 2003/0095374 A1 | 5/2003 | Richardson |
| 2004/0113786 A1 | 6/2004 | Maloney |
| 2004/0215490 A1 | 10/2004 | Duchon et al. |
| 2008/0030345 A1 | 2/2008 | Austin et al. |

(Continued)

OTHER PUBLICATIONS

Sterile iPAD—im PAD Google search documents.

*Primary Examiner* — Neal Sereboff
(74) *Attorney, Agent, or Firm* — Veritay Group, IP; Susan B. Fentres

(57) ABSTRACT

This invention provides a data processing system located within a sterile field. The data processing system includes the elements of a computer with an image capture device configured to acquire information related to a unique device identifier positioned on a medical device located within a sterile field and a sterile enclosure configured to contain the computer with an imaging device. This invention, in one embodiment, provides a system for tracking, confirming and storing patient and procedure information using a unique device identifier hereinafter "a UDI".

4 Claims, 14 Drawing Sheets

(56) References Cited

U.S. PATENT DOCUMENTS

| | | | |
|---|---|---|---|
| 2009/0317002 A1 | 12/2009 | Dein | |
| 2010/0324380 A1* | 12/2010 | Perkins | A61B 5/0002 |
| | | | 600/301 |
| 2011/0246219 A1 | 10/2011 | Smith et al. | |
| 2011/0307274 A1* | 12/2011 | Thompson | G06F 19/327 |
| | | | 705/3 |
| 2012/0166219 A1* | 6/2012 | Mansour | G06F 19/321 |
| | | | 705/3 |
| 2013/0221048 A1 | 8/2013 | Revels et al. | |
| 2013/0222116 A1 | 8/2013 | Barry | |
| 2013/0327826 A1 | 12/2013 | Fleck et al. | |
| 2013/0336554 A1 | 12/2013 | Lewis et al. | |
| 2014/0107471 A1* | 4/2014 | Haider | A61B 17/1703 |
| | | | 600/424 |
| 2014/0263674 A1* | 9/2014 | Cerveny | G06K 19/06028 |
| | | | 235/494 |
| 2015/0026175 A1* | 1/2015 | Nuggehalli | G06F 17/30038 |
| | | | 707/736 |
| 2015/0272694 A1* | 10/2015 | Charles | A61B 1/32 |
| | | | 600/202 |
| 2015/0272894 A1 | 10/2015 | Charles | |
| 2015/0370973 A1* | 12/2015 | Jones | G06F 19/325 |
| | | | 705/2 |
| 2016/0022374 A1* | 1/2016 | Haider | A61B 17/17 |
| | | | 606/96 |
| 2017/0202630 A1* | 7/2017 | Gerstner | A61B 50/15 |
| 2017/0202830 A1 | 7/2017 | Gerstner | |

\* cited by examiner

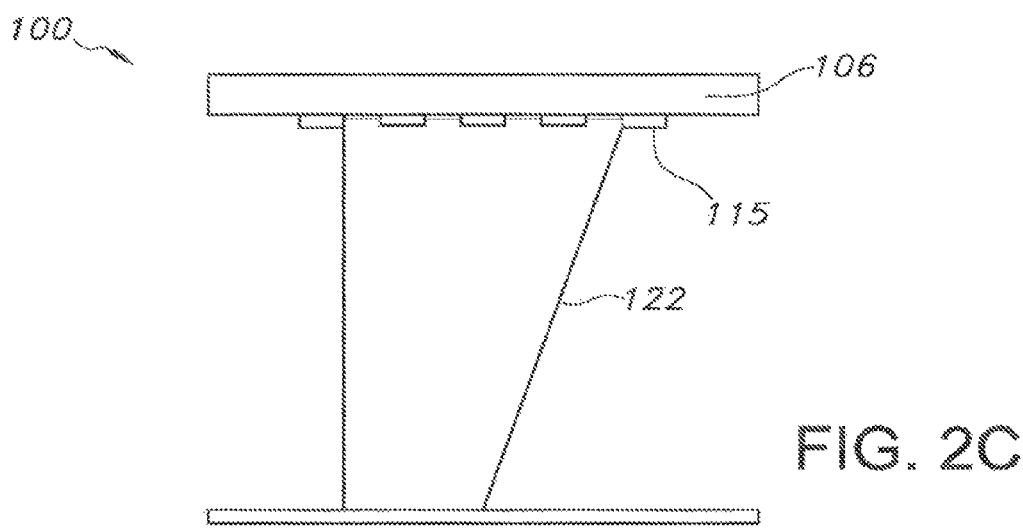

SYSTEM, APPARATUS FOR USE IN A STERILE FIELD AND METHOD FOR TRACKING, CONFIRMING AND STORING PATIENT AND PROCEDURE INFORMATION USING A UNIQUE DEVICE IDENTIFIER ASSOCIATED WITH A MEDICAL DEVICE

CROSS REFERENCE TO RELATED APPLICATIONS

This application is a divisional application of U.S. Ser. No. 15/315,308 filed 30 Nov. 2016, a sec. 371 national stage application of PCT/US16/33877 filed 24 May 2016 and U.S. provisional patent application Ser. No. 62/185,638 filed 28 Jun. 2015 (hereby specially incorporated here by reference).

STATEMENT REGARDING FEDERALLY SPONSORED RESEARCH OR DEVELOPMENT

None.

REFERENCE TO SEQUENCE LISTING, A TABLE FOR A COMPUTER PROGRAM LISTING, COMPACT DISC APPENDIX

None.

BACKGROUND OF THE INVENTION

Field of the Invention

This disclosure relates to a system, apparatus and method for tracking, confirming and storing patient and medical procedure information using a unique device identifier ("UDI") associated with a medical device and information related to the medical device for use in a sterile field.

Description of Related Art Including Information Disclosed Under 37 CFR 1.97 and 1.98

The United States Food and Drug Administration ("FDA") is in the process of establishing a unique device identifier ("UDI") system to identify, track, and allow comparative effectiveness research for all medical devices. When this system is fully implemented, all medical devices will include a unique device identifier ("UDI"). Under the UDI system when fully implemented, the labeler of each medical device labeled with a unique device identifier (UDI) must submit information concerning that device to the FDA to be maintained in the Global Unique Device Identifier Database ("GUDID"). It is contemplated that the UDI will be recorded in a variety of situations, such as for example, point of care in electronic health records. Additionally, it is contemplated that UDIs can be incorporated into hospital inventory management, billing records and administrative transactions.

The pathway to implementation of a UDI system has been characterized as complex. Unique Device Identifier (UDIs); A Roadmap for Effective Implementation, December 2014, Brookings Institution report. U.S. Pat. No. 8,146,825 (Branko Prpa) discloses an assembly including a scanner within a sterile drape that can communicate with a computer. A need exists in the industry to devise a system to use unique device identifier information interactively in a sterile field. One application of this technology is to allow the verification of a medical device, while it is still in the packaging, saving a hospital or clinic the expense associated with opening the packaging of an erroneous medical devices in an operating room.

BRIEF SUMMARY OF THE INVENTION

This invention provides a data processing system located within a sterile field. The data processing system includes the elements of a computer with an image capture device configured to process information related to a unique device identifier positioned on a medical device located within a sterile field and a sterile enclosure configured to contain the computer with an imaging device. This invention, in one embodiment, provides a system for tracking, confirming and storing patient and procedure information using a unique device identifier hereinafter "a UDI". The system includes a frame having a body and a plurality of support legs. The frame is configured to retain a computer apparatus.

In this invention, the computer apparatus includes an application and processor configured to obtain an image of a UDI, to digitize the UDI, to transmit the digitized UDI to a database; to confirm the device with the GUDID database prior to implantation, to increase patient safety and to permanently store the received information in a HIPAA-compliant searchable database. In another embodiment, the application is configured to also incorporate additional patient information independent of the UDI. In one embodiment, the computer with the imaging device is made of one or more computing devices having one or more processors, the one or more processors being configured to: receive a Global Unique Device Identifier Database data to a computer within the sterile field; receive basic patient and medical procedure information; receive a medical device manufacturer and a device type selected by a user, receive an image of a unique device identifier located on a medical device; decode a captured image of the unique device identifier to provide a decoded unique device identifier; identify the medical device by matching a decoded captured image of the Unique Device Identifier with the Global Unique Device Identifier Database data to establish an identity of the imaged device; and compare the identity of the imaged device to the medical device manufacturer and device type selected by the user to verify the imaged device.

In another embodiment, the computer with the imaging device is configured to receive basic patient and medical procedure information; receive a medical device manufacturer and a device type selected by a user; receive an image of a unique device identifier located on a medical device; decode a captured image of the unique device identifier to provide a decoded unique device identifier; transmit decoded image information to a remote a HIPPA-compliant server; receive GUDID data at the remote a HIPPA-compliant server; identifying the device by matching the decoded captured image of the Unique Device Identifier with the Global Unique Device Identifier Database data at the remote HIPPA-compliant server and transmitting this identity to the user, who then compares the identity of the imaged device to the manufacturer and device type selected originally by the user to verify the imaged device.

This invention further provides a frame configured to receive a computer apparatus. The frame is made of a body having a base. The base includes an aperture sized and positioned to expose a camera lens of a computer with an imaging device. To retain and position the computer with an imaging device, the base has a bottom surface and a top surface and two parallel side end surfaces and a back-side surface projecting perpendicularly above the top surface of the base. A back flange is connected to the back-side surface with an open space opposite the back side surface. The open space is configured to receive the computer with an imaging device. The base further includes a plurality of side flanges, each connected to one of a plurality of side end surfaces. Each of the plurality of front side edges form a front end of each of the two parallel side end surfaces. Each of the plurality of side flanges is recessed from each of the plurality of front side edges to form a plurality of front side end surfaces. These elements are configured to keep the computer with an image capture device properly located on the tray once it is inside the sterile enclosure. In addition to the base, the frame also includes a plurality of support legs connected to the base. The plurality of support legs are configured to position the computer with an imaging device to acquire information related to a unique device identifier on a medical device.

This invention further provides a flexible sterile enclosure for receiving and isolating a non-sterile computer apparatus, wherein the flexible sterile enclosure is made of: a container portion having a top and bottom surface, wherein the container portion has a plurality of closed edges and an open section configured to receive the non-sterile computer with an imaging device, and wherein the bottom surface of the container portion has an optical aperture positioned to coordinate with the lens of a camera of non-sterile computer with an imaging device. The sterile enclosure has a folded back flap portion on the bottom surface. The folded back flap portion has two short closed side ends and a top edge and a bottom edge. The bottom edge forms an opening configured to allow the flexible sterile enclosure to contact: the front surface of the frame, a portion of a bottom surface of the frame and a plurality of front side end surfaces of the frame; the flexible sterile enclosure further includes a closure means for sealing the flexible sterile enclosure This invention further provides a method to obtain an image of a unique device identifier involving the steps of: providing a sterile enclosure configured to contain a computer apparatus with an imaging device, wherein the sterile enclosure is made of: a container portion having a top and a bottom surface, wherein the container portion has a plurality of closed edges and an open section configured to receive the computer with an imaging device, wherein the bottom surface of the container portion has an optical aperture positioned to coordinate with a lens of a camera; a folded back flap portion, a central flap and a plurality of side flaps, wherein the plurality of side flaps and the central flap have an adhesive to facilitate the sealing of the sterile enclosure; inserting the sterile enclosure on to a top surface of a frame; wherein the sterile enclosure has an optical aperture surrounded by a gasket; positioning the optical aperture of the sterile enclosure through a frame aperture in a base of the frame to concentrically locate the gasket and the optical aperture with the frame aperture; positioning the folded back flap portion of the sterile enclosure to contact a front surface of the frame and a portion of a bottom surface of the frame and a plurality of front side end surfaces of the frame; positioning the computer with an imaging device within the sterile enclosure to associate the lens of the computer with an imaging device with the optical aperture of sterile enclosure; enclosing the computer with an imaging device within the sterile enclosure by sealing the front flap to the bottom surface of the frame and the plurality of side flaps around a sealed central flap, to the top of the sterile enclosure; and passing a medical device with a unique device identifier under the frame to obtain an image of the unique device identifier.

This invention further provides a method including the steps of: inserting a sterile enclosure on to the top surface of a frame, wherein the sterile enclosure has an optical aperture surrounded by a gasket; positioning the optical aperture of the sterile enclosure through an aperture in a base of the frame, wherein the gasket projects outwardly through the frame, thereby concentrically locating the gasket and the optical aperture with the aperture in the base. The method further includes the steps of: positioning a folded back flap of the sterile enclosure container to contact at the front edge of the top surface of the frame, the bottom surface of the frame and front side edges of the frame. The next steps involves removing a backing strip from an adhesive layer from a front flap and from a plurality of side flaps of the sterile enclosure container, positioning the computer apparatus within the sterile enclosure container, so that a lens of the computer apparatus is associated with the optical aperture of the sterile enclosure container, and enclosing the computer apparatus within the sterile enclosure by sealing the front flap to the bottom surface of the frame and the plurality of side flaps around the sealed front flap to the top of the sterile enclosure. The method further includes the steps of: passing a medical device with a UDI under the frame, obtaining an image of the UDI; digitizing the UDI; transmitting the UDI to a database; and receiving a validation of the medical device at a first location, such as in a clinical setting and at other places such as EHR/EMR, Remote HIPPA-compliant database, or remote labeler/manufacturer database.

This invention further provides a method to identify a medical device in a sterile field by processing an image of a unique device identifier. This method includes the steps of: enclosing a computer apparatus with an imaging device within a sterile enclosure, positioning the computer apparatus in a sterile field, to obtain an image of an unique device identifier on the medical device; identifying the medical device in the sterile field by decoding the unique device identifier to provide an identified medical device; and comparing the identified medical device to data from a Global Unique Device Identifier Database to provide a verified medical device within the sterile field.

The subject matter further includes: a non-transitory computer-readable medium having embodied thereon an at least one application, the at least one application being executable by a processor, to perform a method, the method includes the steps of: receiving a Global Unique Device Identifier Database data to a local computer; receiving basic patient and medical procedure information; receiving a medical device manufacturer and a device type selected by a user; receiving an image of a unique device identifier located on a medical device; decoding a captured image of the unique device identifier to provide a decoded unique device identifier, identifying the medical device by matching a decoded captured image of the Unique Device Identifier with the Global Unique Device Identifier Database data to establish an identity of the imaged device; and comparing the identity of the imaged device to the medical device manufacturer and device type selected by the user to verify the imaged device. The method also includes the step of receiving a designation that the user accepts the verified device for use in the patient and transmitting the accepted unique device identifier to a patient chart in an EHR/EMR system.

The subject matter further includes: a non-transitory computer-readable medium having embodied thereon an at least one application, the at least one application being executable by a processor, to perform a method, the method includes the steps of: receiving a medical device manufacturer and a device type selected by a user, receiving an image of a unique device identifier located on a medical device; decoding a captured image of the unique device identifier to provide a decoded unique device identifier; transmitting decoded image information to a remote a HIPPA-compliant server; receiving GUDID data at the remote a HIPPA-compliant server; identifying the device by matching the decoded captured image Unique Device Identifier with the Global Unique Device Identifier Database data at the remote HIPPA-compliant server and transmitting this identity to the user; and; comparing the identity of the imaged device to the manufacturer and device type selected originally by the user to verify the imaged device. In a further embodiment, the method includes the steps of receiving a designation that the user accepts the verified device for use in the patient; and then transmitting the accepted unique device identifier to a patient chart in an EHR/EMR system.

BRIEF DESCRIPTION OF SEVERAL VIEWS OF THE DRAWING(S)

The invention can be best understood by those having ordinary skill in the art by reference to the following detailed description when considered in conjunction with the accompanying drawings in which:

FIG. 2C illustrates an exemplary embodiment of a side view of the frame.

DETAILED DESCRIPTION OF THE INVENTION

Figure 1:
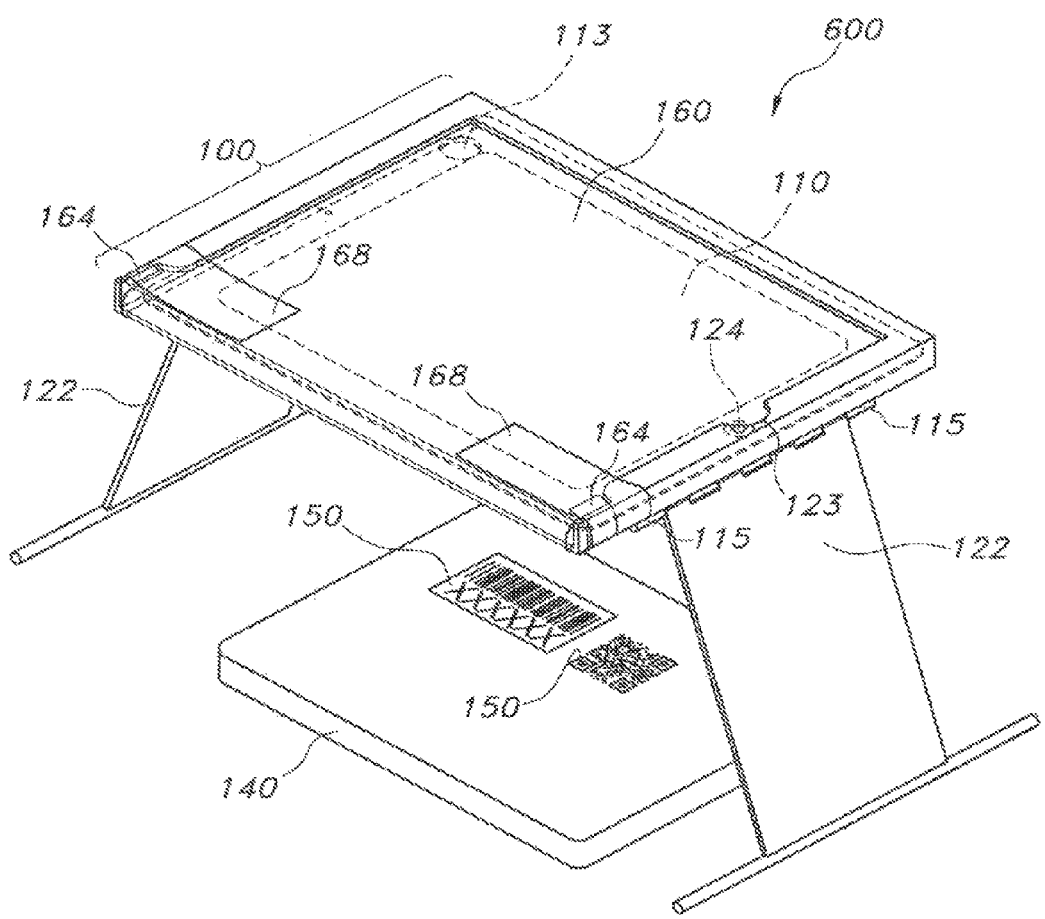
FIG. 1 illustrates exemplary embodiments of an assembly of a frame, with a computer apparatus in a sterile enclosure and a medical device.

The present invention may be understood more readily by reference to the following detailed description of the invention. It is to be understood that this invention is not limited to the specific devices, methods, conditions or parameters described herein, and that the terminology used herein is for the purpose of describing particular embodiments by way of example only and is not intended to be limiting of the claimed invention. Also, as used in the specification containing the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value.

One of the objects of the present technology is to provide an apparatus, system and method for tracking patient and procedure information using a unique device identifier ("UDI") related to a medical device. This invention provides a data processing system located within a sterile field. The data processing system includes the elements of a computer with an image capture device configured to acquire information related to a unique device identifier positioned on a medical device located within a sterile field and a sterile enclosure configured to contain the computer with an imaging device. This invention, in one embodiment, provides a system for tracking, confirming and storing patient and procedure information using a unique device identifier hereinafter "a UDI".

The subject matter includes: a non-transitory computer-readable medium having embodied thereon at least one application, the at least one application being executable by a processor of an application terminal with an imaging device, to perform a method, the method includes the steps of: receiving patient and procedure information, receiving medical device manufacturer and device type selected by a user, receiving an image of a unique device identifier located on a device present in a sterile setting, the image of a unique device identifier is captured with a computer with an imaging device; and decoding a captured image of the unique device identifier to provide a decoded unique device identifier for the device in the sterile setting. The decoded information is compared to the GUDID and the medical device imaged is identified. The identified device is then compared to the patient specific procedure and device information input by the user. The medical device can then be accepted or rejected by the user. When accepted, the UDI is transmitted for permanent inclusion in the patient's EHR/EMR. In addition the accepted UDI and certain patient and procedure specific information is transmitted to a remote HIPPA-compliant data repository for later use. The accepted UDI and certain other patient and procedure information is transmitted to the appropriate labeler/manufacturer database to comply with FDA regulations.

Referring to FIG. 1, an illustrative embodiment is provided showing the assembly of the frame 100 configured to retain a computer with an imaging device 110. The computer with an imaging device 110 is sealed in a sterile enclosure 160. The computer with an imaging device 110 can be, for example, a computer apparatus with digital image capture capability. This computer with an imaging device 110 may be specially constructed for the required purposes, or it can be a general-purpose computer selectively activated or reconfigured by an application program stored in the computer with an imaging device 110 to process information. Such an application program may be stored in a computer readable storage medium such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, which can be coupled to a computer system bus. The computer with an imaging device 110 includes a processor, and a memory communicatively coupled to the processor, the memory storing instructions executable by the processor to perform a method as delineated in an application. The computer with an imaging device 110 also includes a server that functions to serve business logic to the application through any number of protocols. The computer can exist in many different forms, such as for example, laptop computers, tablets, glasses, goggles and terminals.

The present invention also relates to a computer with an imaging device 110 for performing the operations herein. A computer with an imaging device 110 is a device that accepts information (in the form of digitized data) and manipulates it for some result based on a program or sequence of instructions on how the data is to be processed. The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear as set forth in the description below. In addition, the present invention is not described with reference to any particular programming language. It will be appreciated that a variety of programming languages may be used to implement the teachings of the invention as described herein.

The present invention includes a machine-accessible medium having stored thereon instructions, which may be used to program a computer system (or other electronic devices) to perform a process according to the present invention. A machine-accessible medium includes any device for storing or transmitting information in a form readable by a machine (e.g., a computer). For example, a machine-accessible (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., carrier waves, infrared signals, digital signals, etc.). This invention further provides a programming application which can be used on an internet and image capable computer device. The application is able to connect to multiple servers, allowing the digitized information to be validated by a user and saved to a manufacturer or labeler and government databases and to be used in research and patient care.

In one embodiment, the computer with an imaging device 110 is an IPAD (Apple Inc., Cupertino Calif.). The digital image capture capability is provided, in one illustrative example, as a camera having a lens. A camera captures an image of a unique device identifier 150, such as a bar code and/or a 2D matrix or similar identifier and the data processing system digitizes the image into a computer readable format. The frame 100 is configured to position the computer with an imaging device 110 to obtain an image of a medical device 140. These images include a unique device identifier of the medical device 140.

An assembly 600 includes the frame 100 holding a computer with an imaging device 110, enclosed in the sterile enclosure 160. This view of the assembly 600 shows a plurality of side flaps 168 and a portion includes a folded back flap portion 164 that is part of the sterile enclosure 160. The plurality of side flaps 168 and the folded back flap portion 164 of the sterile enclosure 160, are configured to seal the sterile enclosure 160, enclosing the computer with an imaging device 110 within the sterile enclosure 160 to allow the computer with an imaging device 110 within the sterile field.

Figure 2A:
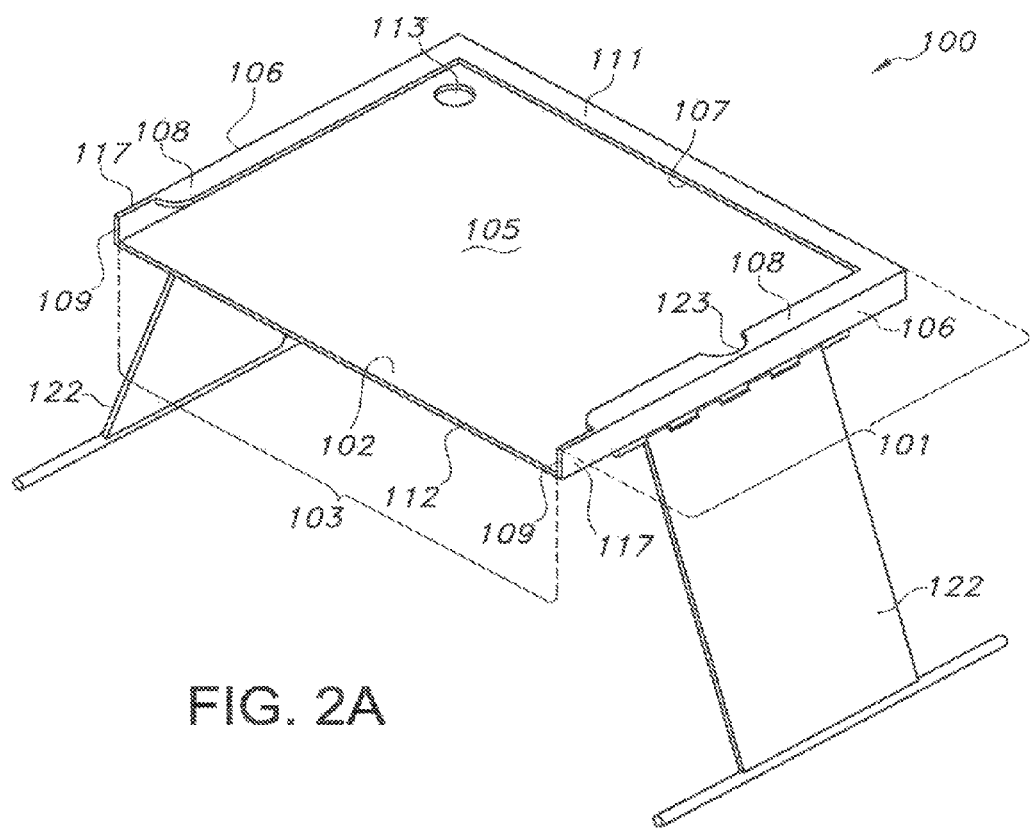
FIG. 2A illustrates an exemplary embodiment of a frame.
Figure 2B:
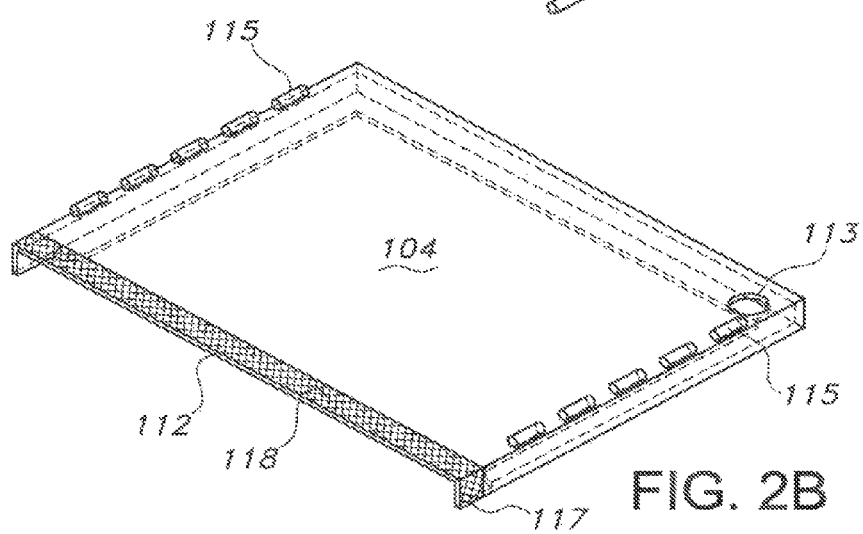
FIG. 2B illustrates an exemplary embodiment of a bottom surface of the frame.

Now referring to FIGS. 2A-2C, the frame 100 is made of a body 101 having a base 102 configured to support the computer with an imaging device 110. In this exemplary embodiment, the base 102 has a bottom surface 104 and top surface 105. Projecting perpendicularly above the top surface 105 of the base 102, are a plurality of parallel side end surfaces 106 and a back side surface 107. Each of a plurality of front side edges 109 form the front end of each of the two parallel side end surfaces 106. The space opposite the back side surface 107 is an open space 103. The open space 103 is configured to receive the computer with an imaging device 110. A front surface 112 extends between the plurality of front side end edges 109. The front side end surface 117 of the plurality of side end surfaces 106 terminates at the plurality of side flanges 108. A plurality of side flanges 108 are recessed from the front side edges 109 and each of the plurality of side flanges 108 are substantially perpendicular to each of the parallel side end surfaces 106 and they project inwardly to retain the computer with an imaging device 110.

In an exemplary embodiment, each of the plurality of the side flanges 108 are recessed from the front side edge by about 20 mm. A back flange 111 extends the length of the back-side surface 107 and it projects inwardly to retain the computer with an imaging device 110. In one exemplary embodiment, the plurality of side flanges 108 and back flange 111 do not contact each other, although in another embodiment the flanges can be contiguous as shown in FIG. 2A. A cut-out 123 can be provided to access a home button 124 of a computer with an imaging device 110.

Now referring to FIG. 2B, a view of the bottom surface of the frame is shown. By way of illustration, the front area 118 of bottom surface 104 (shown as a cross-hatched section) extends in one exemplary embodiment back about 2 cm from the edge of front surface 112 of the frame 100. This figure shows a view of first front side end surface 117 of the each of the plurality of side end surfaces 106 terminates at the plurality of side flanges 108 (shown as a cross-hatched section). The cross-hatched sections 117 and 118 are configured to be covered by the folded back flap 164 of a flexible sterile enclosure 160 shown in FIG. 3A-4B. The contact between cross-hatched sections 117 and 118 and the flexible sterile enclosure 160 facilitates the formation of a sterile barrier to allow the computer with an imaging device 110 into a sterile setting.

The frame 100 is preferably made of a metal or plastic material that can be sterilized. The frame 100 is made of a material having sufficient strength to hold the computer with an imaging device 110 without bending or flexing, to prevent blurring of the image of the unique device identifier 150.

In one embodiment, the computer with an imaging device 110 is an IPAD (Apple Inc., Cupertino, Calif.) and the frame 100 has an aperture 113 sized and positioned to expose the lens of the computer with an imaging device 110. The aperture 113 is sized and positioned based on the design of the computer with an imaging device 110.

The frame 100 has a plurality of support legs 122 to position the computer with an imaging device 110 above a medical device 140 with unique device identifier 150 inscribed, imprinted, etched or affixed onto the medical device 140 or on the related packaging. In one embodiment shown in FIG. 2A, the plurality of support legs 122 are positioned at 110 degrees relative to the plane (of the base 102) to increase the stability of the frame 100. The height of the plurality of the support legs 122 relate to the size of the medical device 140 placed under the frame 100 and the length can be variable depending on the size of the medical device to be imaged. In one embodiment, the computer with an imaging device 110 is an IPAD (Apple Inc., Cupertino, Calif.), in this embodiment, the height of the plurality of legs 122 is about eight inches. In an alternative embodiment, shown in FIG. 2C one of the pluralities of support legs 122 has a beveled edge to prevent obstruction of the field of view of the computer with an imaging device 110. The plurality of legs 122 can be attached, for example, to the bottom surface of the base 104, or the two parallel side end surfaces 106, by a hinge or attachment point 115, to the frame 100 or the side surface 107.

Figure 3A:
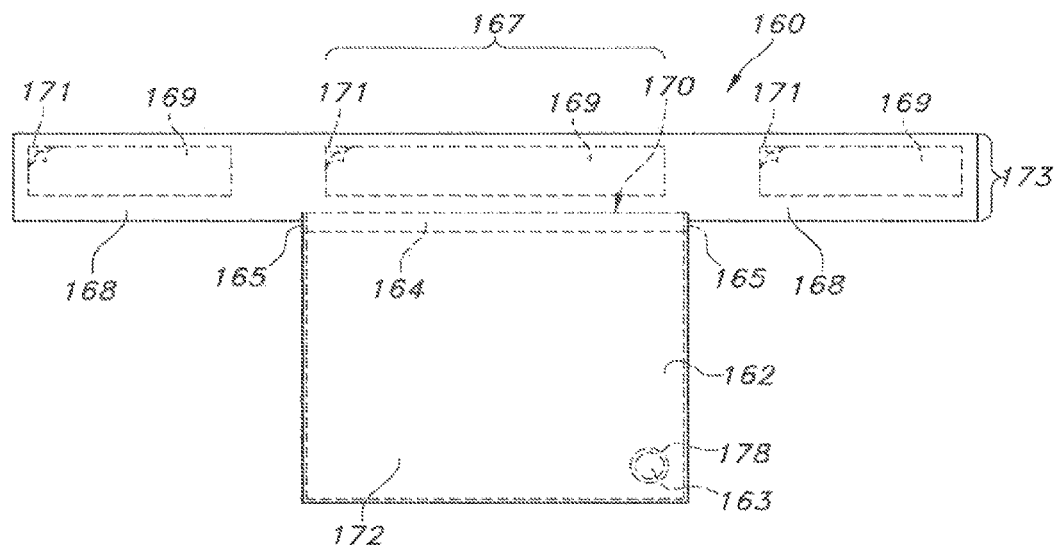
FIG. 3A illustrates a top view of an exemplary embodiment of a sterile enclosure container.
Figure 3B:
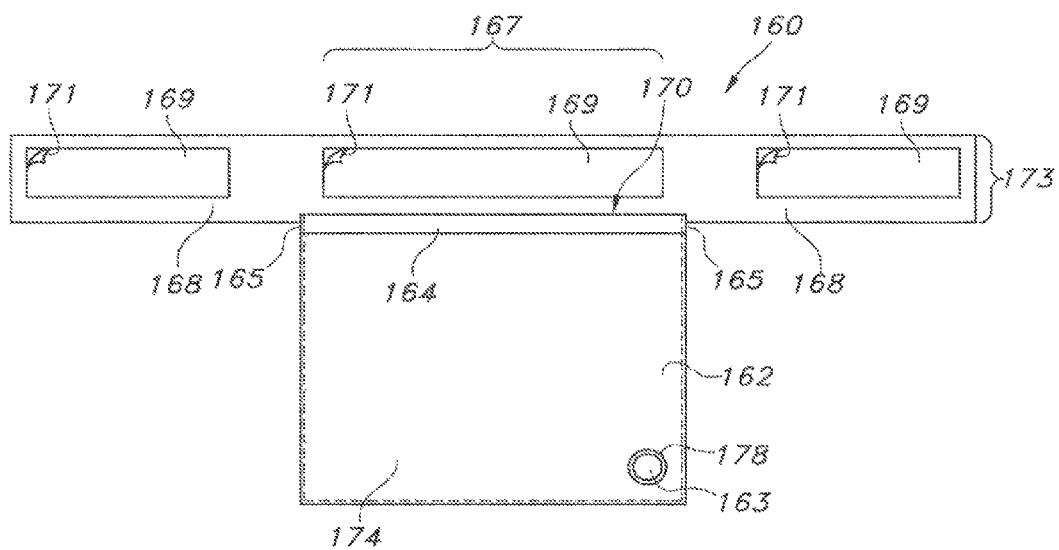
FIG. 3B illustrates a bottom view of an exemplary embodiment of a sterile enclosure container.

Now referring to FIGS. 3A-3B, a flexible sterile enclosure 160 is provided. The sterile enclosure 160 provides a sterile barrier into which a person, whose hands are scrubbed/sterile, can receive the non-sterile item, such as a computer with an imaging device 110, without compromising the sterility of the exterior of the barrier. This step requires a second person (not shown) who is non-sterile to assist the person who is sterile.

In an exemplary embodiment, the flexible sterile enclosure 160, in this embodiment, is generally "T" shaped and is made of a container portion 162, a closure device 173, a flap portion 168 and a folded back flap portion 164. The flexible sterile enclosure 160 is preferably formed from one piece of plastic film, preferably polyethylene film. The container portion 162 has an opening 170 sized to accommodate the computer with an imaging device 110. The container portion 162 is closed on three sides and is sized to receive the computer with an imaging device 110. The container portion 162 has a top surface 172 and a bottom surface 174. An optical aperture 163 is located on the bottom surface 174 of the container portion 162 of the flexible sterile enclosure 160. The optical aperture 163 is a section in the wall of the sterile enclosure 160 that is optically clear. The optical aperture 163 is surrounded by the gasket 178.

Figure 4A:
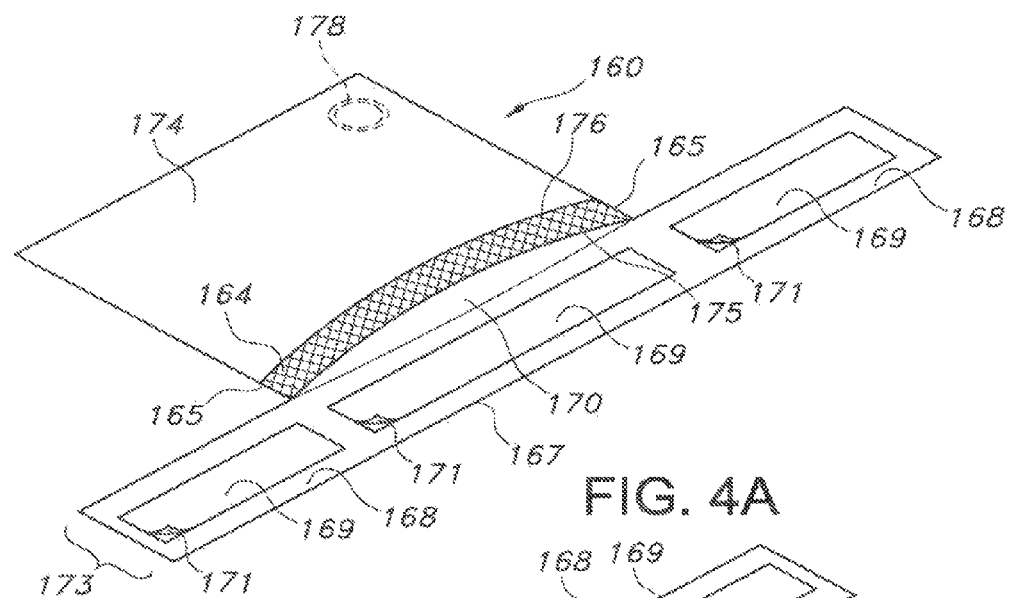
FIG. 4A illustrates a bottom view of an exemplary embodiment of the sterile enclosure container showing the enclosure opening.
Figure 4B:
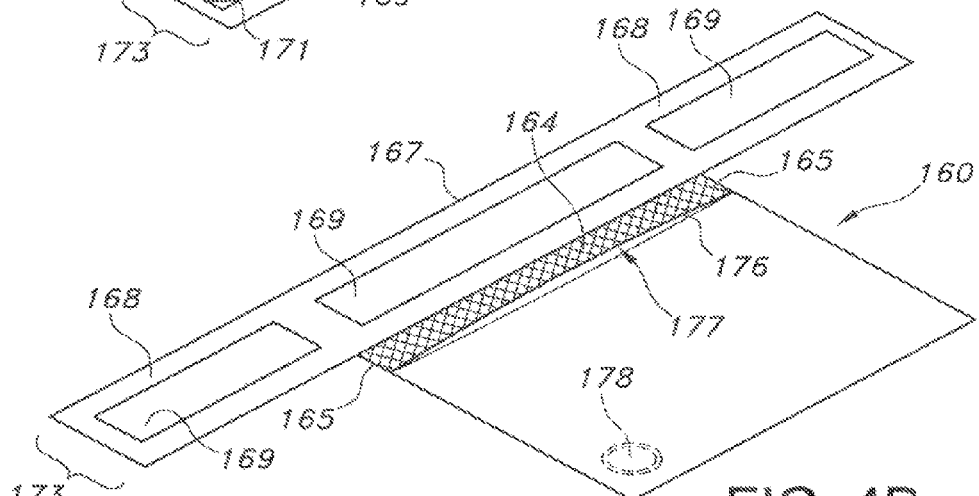
FIG. 4B illustrates a bottom view of an exemplary embodiment of the sterile enclosure container showing the folded back flap opening.

Now referring to FIGS. 4A-4B, in an exemplary embodiment, the bottom surface 174 of the sterile enclosure 160 includes a folded back flap portion 164 (shown as a cross-hatched section) that is folded back and closed on two short side ends 165. The folded back flap portion 164 has a top edge 175 that forms a portion of enclosure opening 170. The folded back flap portion 164 has a bottom edge 176. The bottom edge 176 and the two short side ends 165 of the folded back flap portion 164 serves to form an opening 177.

Figure 6A:
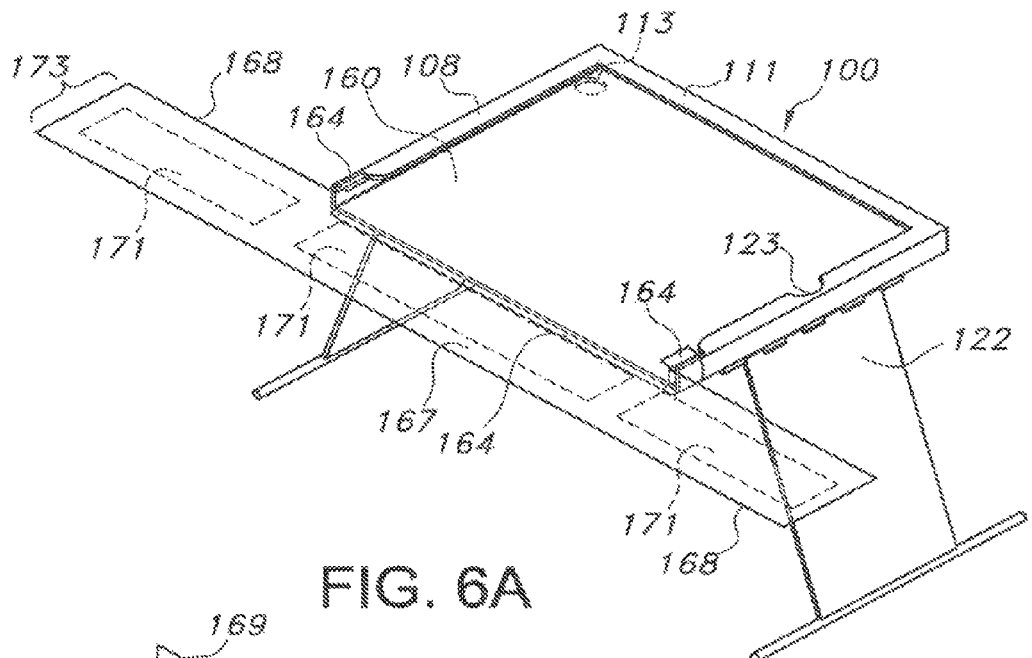
FIG. 6A illustrates a top perspective view of an exemplary embodiment of a sterile enclosure and frame.
Figure 6B:
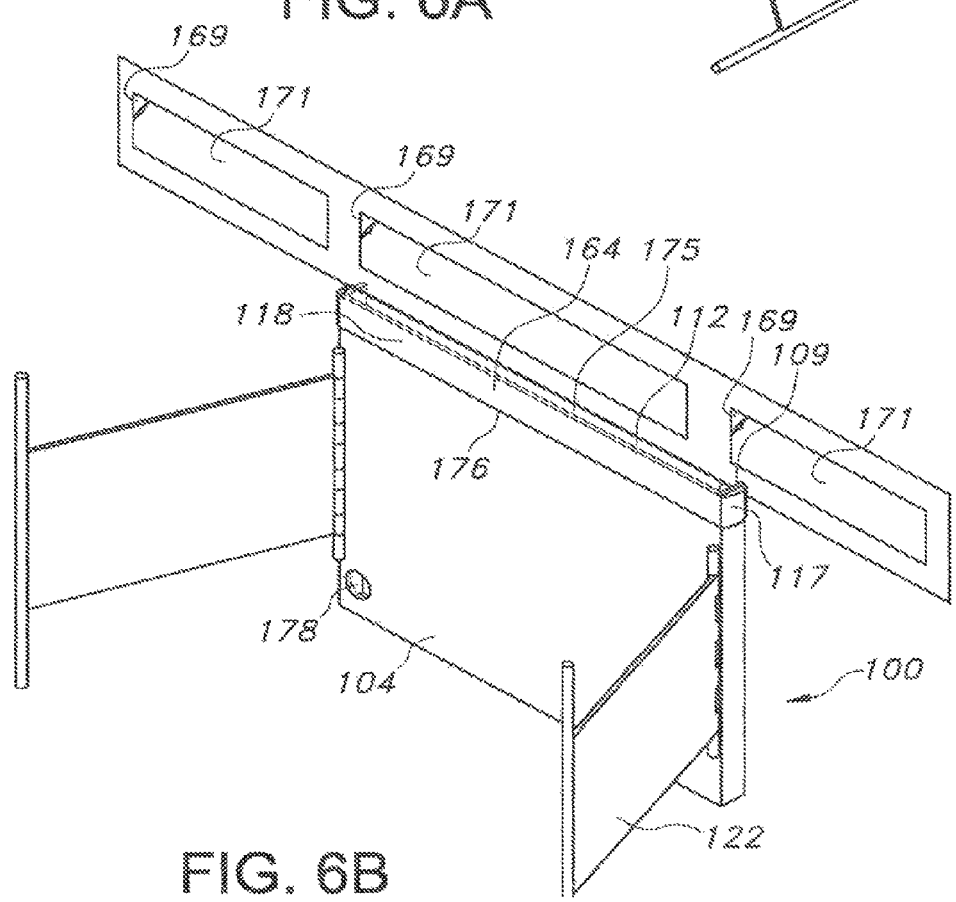
FIG. 6B illustrates a bottom perspective view of an exemplary embodiment of a sterile enclosure and frame.

Now referring to FIG. 6B, the folded back flap portion 164 surrounds the front surface 112 of frame 100 and the plurality of front side end edges 109 of the frame 100. The front area 118 of bottom surface 104 of frame 100 extends in one exemplary embodiment back about 2 cm from the edge of front surface 112 of the frame 100. The front edge surface 117 of the each of the plurality of side end surfaces 106 terminates at the plurality of side flanges 108. Sections 117 and 118 are configured to be covered by the folded back flap 164 of a flexible sterile enclosure 160. The contact between sections 117 and 118 and the flexible sterile enclosure 160 facilitates the formation of a sterile barrier to allow the computer with an imaging device 110 into a sterile setting.

The sterile enclosure 160 has a closure device 173, which in an exemplary embodiment includes a plurality of side flaps 168. The plurality of side flaps 168 include an adhesive 169 and associated release liner 171 proximal to the side of the sterile enclosure with the opening. The closure device 173 also includes a central flap 167 positioned between the plurality of side flaps 168. The central flap 167 includes an adhesive 169 and associated release liner 171 proximal to the side of the sterile enclosure 160 with the opening.

Figure 5:
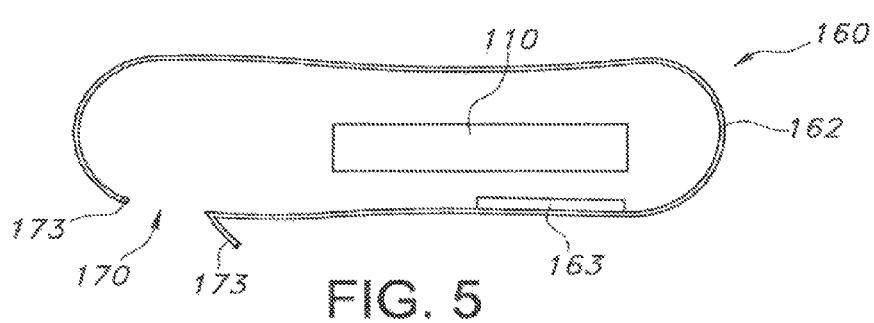
FIG. 5 illustrates an alternative exemplary embodiment of a sterile enclosure container.

Now referring to FIG. 5, an alternative embodiment, sterile enclosure 160 is provided. The sterile enclosure 160 is made of a body of the enclosure, wherein at least a portion of the body of the sterile enclosure 160 is optically clear and another portion, is an opening 170 configured to receive the computer with an imaging device 110, wherein the opening 170 includes a closure device 173 to allow the opening 170 to seal, thereby sealing the computer with an imaging device 110 into the sterile enclosure 160 and allowing the computer with an imaging device 110 into a sterile field. The closure device 173 can be for example, VELCRO tabs positioned on the sterile enclosure 160 to facilitate a seal.

Now referring to FIGS. 6A-6H, an exemplary embodiment shows the process to position the sterile enclosure 160 on frame 100. This process involves the steps of: inserting the sterile enclosure 160 on to the top surface 105 of the frame 100. The top edge 175 of folded back flap portion 164 of the sterile enclosure 160 is placed adjacent to the front surface 112 of the base 102 of frame 100. The folded back flap portion 164 envelops the plurality of front side edges 109 of the frame 100 and also bottom surface 104 of the frame 100. The folded back flap portion 164 contacts the bottom surface 104 of frame 100 on surface 118 and also the outside surface 117 of two parallel side end surfaces 106 of the frame 100.

FIG. 6A shows a top view of the sterile enclosure 160 on frame 100 and FIG. 6B shows a bottom view of the sterile enclosure 160 on frame 100. The bottom surface 174 of the sterile enclosure 160 has a folded back flap portion 164 that is folded back and closed on two short side ends 165. The folded back flap portion 164 has a top edge 175 that forms a portion of enclosure opening 170. The folded back flap portion 164 has a bottom edge 176. The bottom edge 176 and two short side ends 165 of the folded back flap portion 164 surround the front surface 112 of frame 100 and the plurality of front side end edges 109 of the frame 100. The front area 118 of bottom surface 104 of frame 100 extends in one exemplary embodiment back about 2 cm from the edge of front surface 112 of the frame 100. The front edge surface 117 of the each of the plurality of side end surfaces 106 terminates at the plurality of side flanges 108. The sections 117 and 118 are configured to be covered by the folded back flap 164 of a flexible sterile enclosure 160. The contact between sections 117 and 118 of the frame (FIG. 2A) and the flexible sterile enclosure 160 facilitates the formation of a sterile barrier to allow the computer with an imaging device 110 into a sterile setting.

Figure 6C:
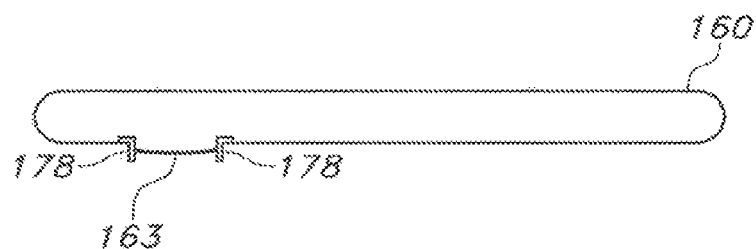
FIG. 6C illustrates a side-view of an exemplary embodiment of a sealed sterile enclosure.
Figure 6D:
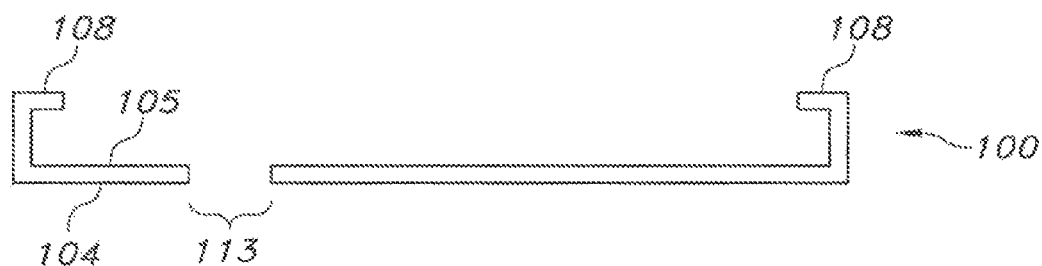
FIG. 6D illustrates a side-view of an exemplary embodiment of the frame.
Figure 6E:
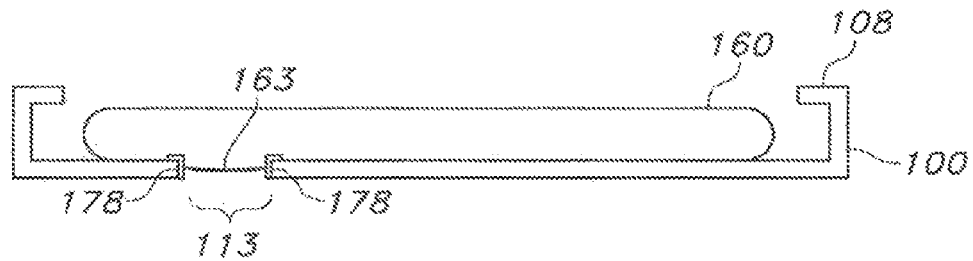
FIG. 6E illustrates a sectional-view of an exemplary embodiment of the enclosure and the frame, taken at A-A from FIG. 6F.
Figure 6F:
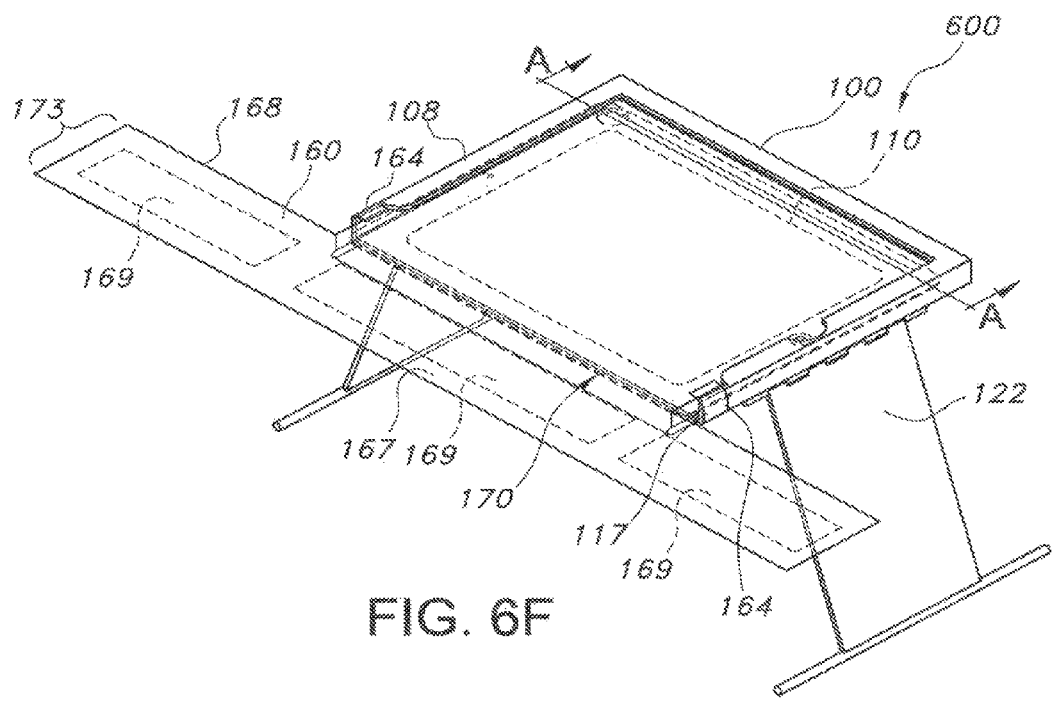
FIG. 6F illustrates top perspective view of an exemplary embodiment of a sterile enclosure enclosing a computer with an imaging device positioned on a frame.
Figure 6G:
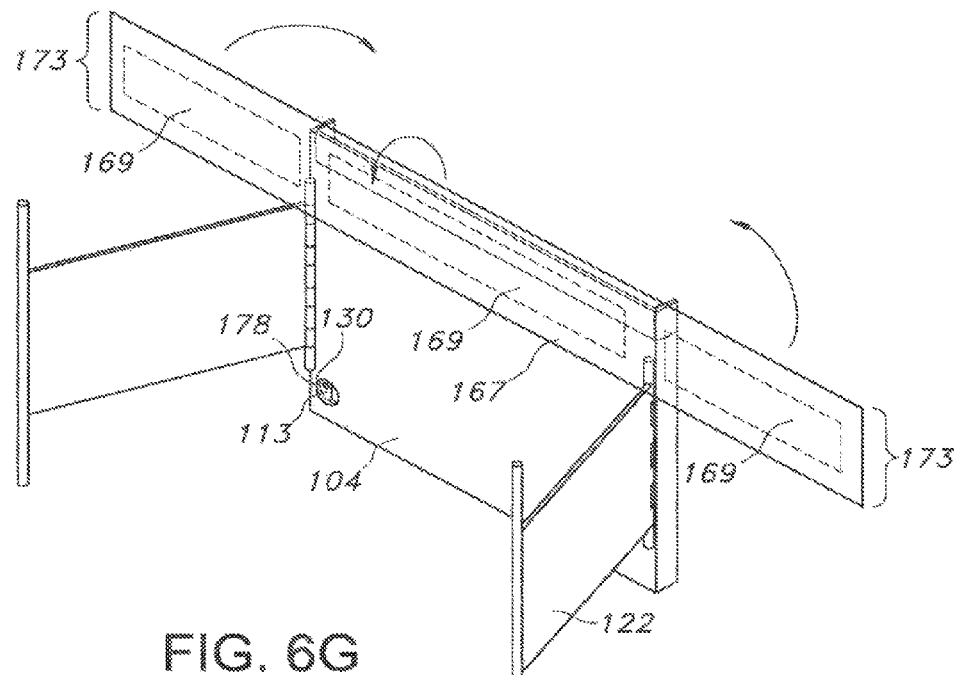
FIG. 6G illustrates bottom perspective view of an exemplary embodiment of a sterile enclosure enclosing a computer with an imaging device positioned on a frame.
Figure 6H:
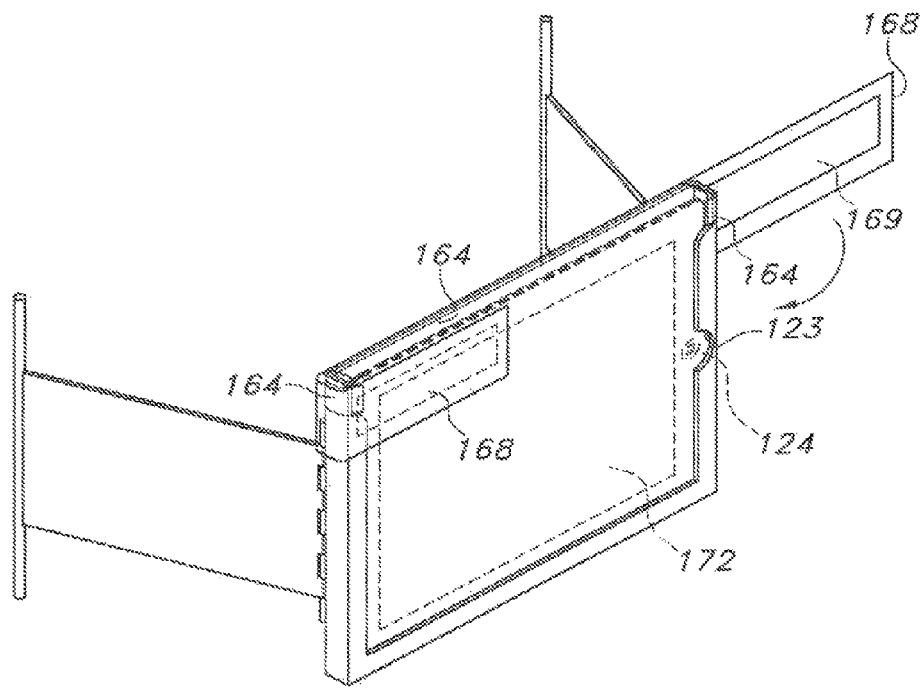
FIG. 6H illustrates side perspective view of an exemplary embodiment of a sterile enclosure enclosing a computer with an imaging device positioned on a frame.

Now referring to FIGS. 6C-6E, in this embodiment, a gasket 178 is integral with the sterile enclosure 160. An optical aperture 163 of the sterile enclosure container 160 is surrounded by the gasket 178. When the optical aperture 163 of the sterile enclosure 160 is positioned through the aperture 113 in base 102 of the frame 100, the gasket 178 projects outwardly through the frame 100, thereby concentrically locating the gasket 178 and the optical aperture 163 with the aperture 113 in the base 102. In the exemplary embodiment, the sterile enclosure 160 provides an optical aperture 163. The optical aperture 163 is provided to ensure that the sterile enclosure 160 has sufficient clarity to allow a digital image to be acquired using the computer with an imaging device 110. The optical aperture 163 can be the wall of the bag itself, when the sterile enclosure 160 is made from sufficiently optically clear flexible material.

Alternatively, the optical aperture 163 may be a discrete flexible or rigid window attached across an aperture in the wall of the sterile enclosure 160. In this embodiment, a gasket 178 forms a mechanical seal with the optically clear material that is different from the wall of the sterile enclosure and fills the space between two or more mating surfaces, is integral with the sterile enclosure 160. When the assembly of the frame 100, sterile enclosure 160 and computer with an imaging device 110 is formed, the gasket 178 is sized to fit through the aperture 113 in frame 100.

Now referring to FIG. 6E-H, the computer with an imaging device 110 is placed in the sterile enclosure 160 through the container portion opening 170. If the computer with an imaging device 110 has a lens 130, the lens 130 is positioned with respect to the optical aperture 163 to allow a digital image to be acquired using the computer with an imaging device 110. The opening 177 of the folded back flap portion 164 facilitates the addition of the computer with an imaging device 110 into the sterile enclosure 160. This occurs when folded back flap portion 164 encloses the front surface 112 and plurality of side ends 109. In an illustrative embodiment, the computer with an imaging device 110 is an IPAD (Apple Inc., Cupertino, Calif.). The sterile enclosure 160 is the size of the frame 100 and the frame 100 is large enough for the sterile enclosure 160 to cover the IPAD (Apple Inc., Cupertino, Calif.).

A scrub technician removes the release liner 171 from the adhesive layer 169, on the central flap 167 and the plurality of side flaps 168 of the sterile enclosure 160 after the computer with an imaging device 110 is placed inside the enclosure by a non-sterile technician. The scrub technician encloses the computer with an imaging device 110 inside the sterile enclosure 160. The central flap 167 is of a sufficient length to contact the bottom surface 104 of the base 102. The adhesive layer 169 of the central flap 167 contacts the bottom surface 104 of the base 102 to form a seal. In an alternative embodiment, a single adhesive layer can be provided rather than discrete strips. In an alternative embodiment, the adhesive layer 169 of the central flap 167 contacts the bottom surface 104 of the base 102 and the folded back flap 164 to form a seal.

In this illustrative embodiment, the plurality of side flaps 168 wrap back on to the sterile enclosure 160 to top surface 172. The plurality of side flaps 168 are of sufficient length to contact top surface 172 of the enclosure 160. The adhesive layer 169 of the plurality of side flaps 168 contacts the sterile enclosure 160. The enclosure opening 170 of the container portion 162 is sealed when the central flap 167 attaches to the bottom surface 104 of the base 102 (and the side flaps 168 seal to the top surface 172 (of the enclosure 160) to seal the opening 170 in the sterile enclosure 160.

Now referring to FIG. 1, a view of the final assembly 600 is shown. An assembly 600 includes the frame 100 holding a computer with an imaging device 110 enclosed in sterile enclosure 160. The plurality of support legs 122 can be folded down and the assembly of computer with an imaging device 110 within the sterile enclosure 160, positioned within the frame 100, is now ready for use to capture an image of a unique device identifier 150 inscribed, etched, imprinted, or affixed onto the medical device 140. In an illustrative embodiment, the computer with an imaging device 110 is an IPAD (Apple Inc., Cupertino. Calif.). In this embodiment, the camera of the computer with an imaging device 110 is located near the corner of the apparatus 110. The aperture 113 in base 102 of the frame 100 is a cutout near the corner of the frame 100. When the optical aperture 163 of the sterile enclosure 160 is positioned through the aperture 113 in base 102 of the frame 100, the gasket 178 projects outwardly through the frame 100, thereby concentrically locating the gasket 178 and the optical aperture 163 within the aperture 113 in the base 102.

Figure 7:
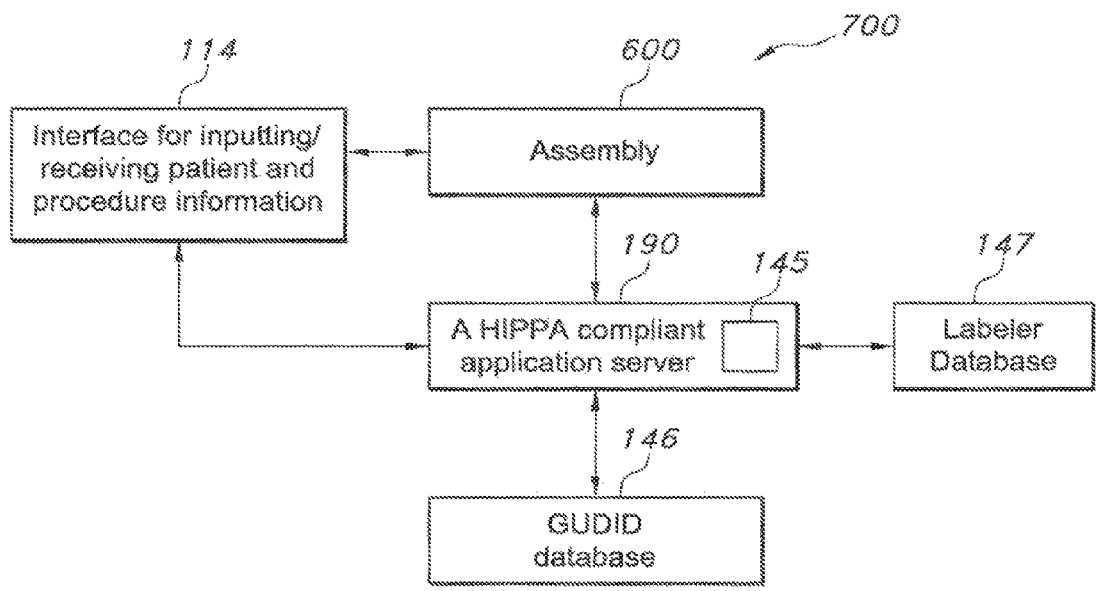
FIG. 7 shows an embodiment of the system elements of the present invention.
Figure 9A:
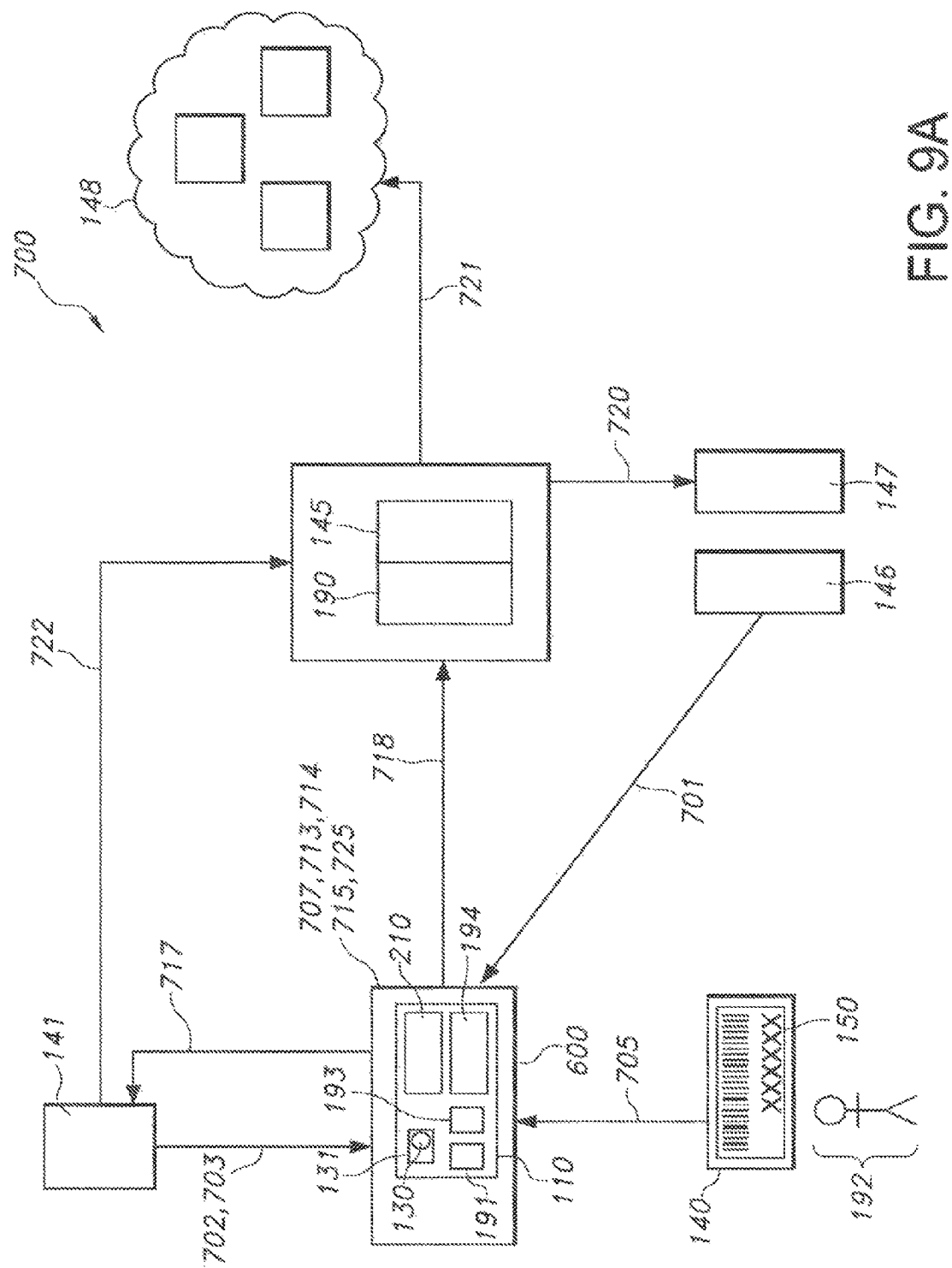
FIG. 9A illustrates an exemplary embodiment of a flow chart of the system.
Figure 9B:
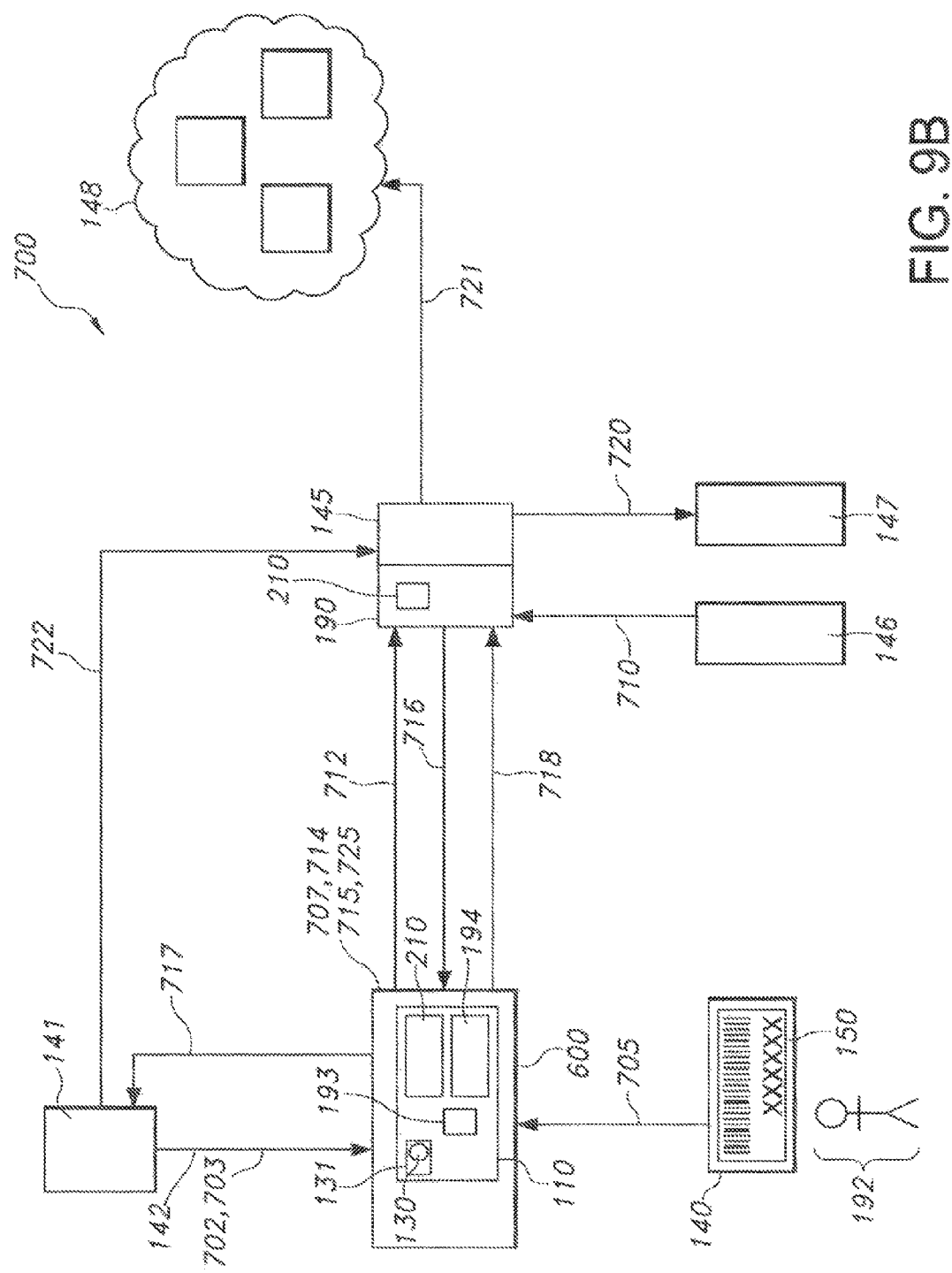
FIG. 9B illustrates an exemplary embodiment of a flow chart of the system.

Now referring to FIG. 7, the data processing system 700 with internet connectivity is provided. A data processing system 700 is a combination of machines, devices, people, and processes that for a set of inputs produces a defined set of outputs. In one exemplary embodiment, the data processing system 700 includes: an interface 114 for inputting patient and procedure information to the system 700; an assembly 600 (as shown in FIG. 1) includes the frame 100 holding a computer with an imaging device 110 enclosed in sterile enclosure 160. The computer with an imaging device 110 also contains a local HIPPA-compliant local server 193 and a computer program product 210 (as shown in FIG. 9A). A HIPAA-compliant remote application server 190 and data repository 145; and a GUDID database 146 can be part of the data processing system 700 (as shown in FIG. 9B). The term "patient information" includes basic patient information that is up-loaded into the system 700 and includes: name, DOB, SSN, etc. which in one embodiment can ultimately be housed in a labeler database 147. In another embodiment, other types of patient information are included like patient age, comorbidities, information of past medical history for an individual patient that will be useful to have in the remote HIPPA-compliant data base that can be maintained for research purposes.

Figure 8A:
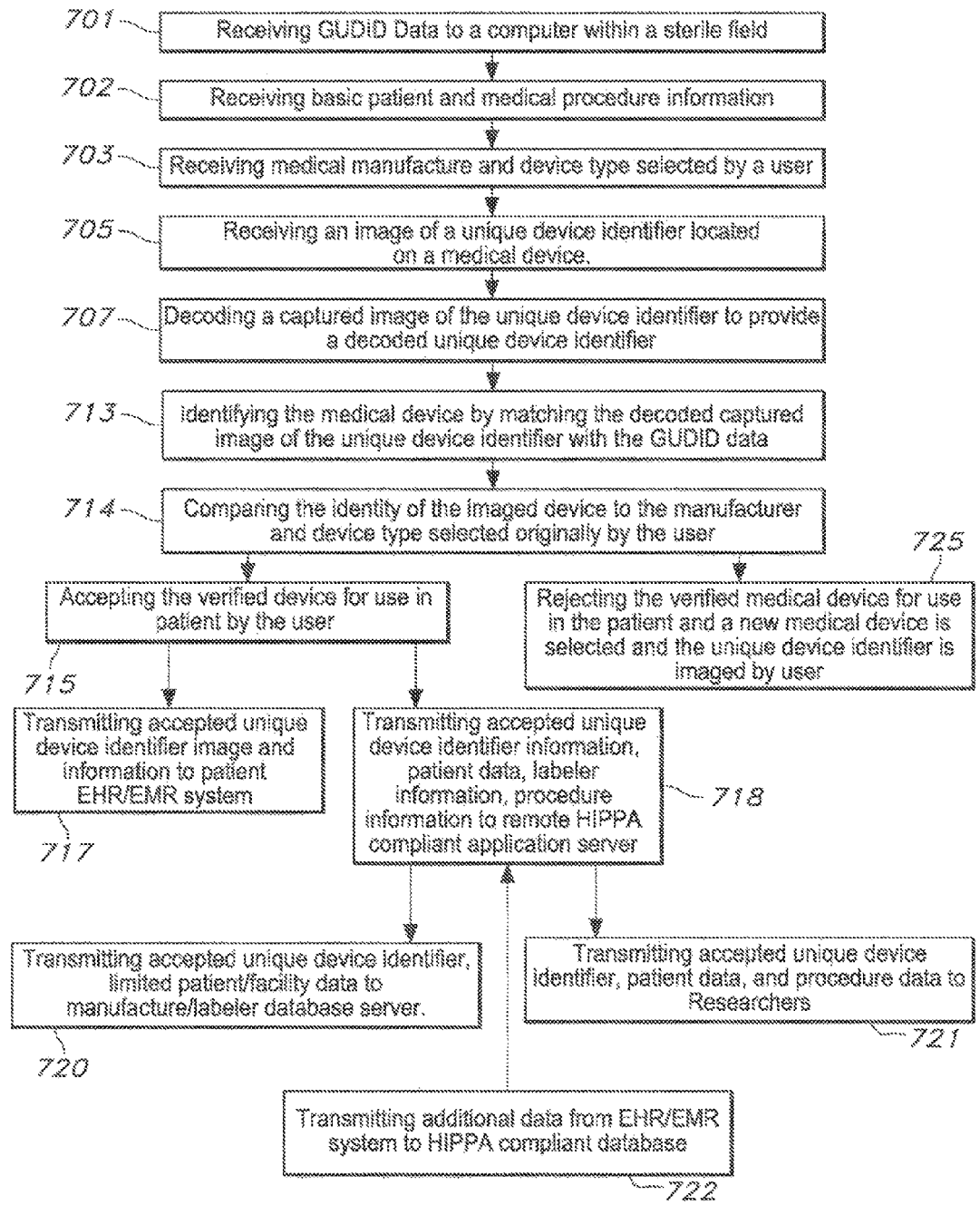
FIG. 8A shows an embodiment of the process steps of the present invention in the embodiment of GUDID data loaded on to a local computer.

Now referring to FIGS. 8A and 9A, a non-transitory computer-readable medium having embodied thereon an application 210, the program being executable by a processor to perform a method is provided. In this embodiment, the method is conducted using a computer with an imaging device 110 such as an IPAD (Apple Inc., Cupertino, Calif.) in system 700. The digital image capture capability is provided in one illustrative example as a camera 131. A camera 131 with a lens 130 captures an image of a unique device identifier 150 and the data processing system of the computer with an imaging device 110 digitizes the image into a computer readable format. A non-transitory computer-readable medium having embodied thereon an at least one application, the at least one application being executable by a processor, to perform a method, the method involves the steps of: receiving a Global Unique Device Identifier Database data to a computer within the sterile field (Step 701);

receiving basic patient and medical procedure information (Step 702); such as patient name, date of birth, facility name, and procedure date; receiving medical device manufacturer and device type selected by a user (Step 703); receiving an image of a unique device identifier located on a medical device present in a sterile setting, the image of a unique device identifier is captured with a computer with an imaging device (Step 705); and decoding a captured image of the unique device identifier to provide a decoded unique device identifier for the device in the sterile setting (Step 707).

The method can further include the steps of: identifying the medical device by matching the decoded captured image of the UDI affixed to the medical device with the received Global Unique Device Identifier Database data (Step 713); comparing the identity of the imaged device to the manufacturer and device type selected originally by the user to verify the imaged device (Step 714). The step of comparing the identity of the imaged device to the manufacturer and device type selected originally by the user to verify the imaged device can involve, in one embodiment, the use of object recognition software using computer vision-based object recognition. Various methods are known to one skilled in the art, such as for example U.S. Pat. Nos. 9,332,149; 8,861,868 8,553,989; or commercially available software such as SENTISIGHT SDK (Neurotechnology Vilnius, Lithuania). In another exemplary embodiment, involves projecting an image of the device associated with the UDI to the user. The method can further include the steps of: requiring the user to accept (Step 715) or reject (Step 725) the medical device for use in the patient thereby receiving a designation that the user accepts the verified device for use in the patient (Step 715) or receiving a designation that the user rejects the verified device for use in a patient, and a new medical device is selected by the user (Step 725) and transmitting only the accepted unique device identifier to a patient chart in an EHR/EMR system (Step 717). The information sent to the EMR/EHR includes the actual captured image of the accepted medical device in addition to the UDI information. According to this method, someone reviewing the medical record could identify the device without having to refer to a UDI database to visually identify the implanted device that corresponds with the UDI. The method can further include the steps of: receiving a designation of the accepted unique device identifier, patient data, labeler information, and procedure information to the HIPPA compliant application server (Step 718). The method can further include the steps of: transmitting the accepted unique device identifier, patient data, and facility data to a manufacturer or a labeler database server (Step 720).

The method can further include the steps of: receiving a designation of the accepted unique device identifier, patient data, labeler information, and procedure information to the HIPPA compliant application server (Step 718). The method can include the step of; receiving additional patient data from EMR/EHR to HIPPA compliant data base such as co morbidities, smoking history, and prior surgeries. (Step 722). The method can further include the steps of: transmitting the accepted unique device identifier, patient data, and facility data to a manufacturer or a labeler database server (Step 720) or the method can further include the step of: transiting the accepted unique device identifier, patient data, and procedure data to researchers (Step 721).

In one illustrative embodiment, a computer with an imaging device 110 is located within the sterile operating field of use. The computer with an imaging device 110, includes a software application 210 also referred to as a computer program product, a database 191, and a HIPAA-compliant local server 193. The computer with an imaging device 110 is configured to acquire information related to a unique device identifier 150 associated with a medical device 140. The local server 193 provides the output to either a web server and/or to the display portion 194 of computer with an imaging device 110 for the User 192 to view while in the procedure or operating room. The output can be an accepted medical device based on the unique device identifier and the previously determined patient and procedure information Steps 702, 703. If the medical device is rejected Step 725, a new medical device is chosen and imaged and the process repeats until the device is accepted by the user 192.

In an exemplary embodiment, the patient and procedure information data is located in an electronic medical record "EHR/EMR" 141. Depending on the EHR/EMR system, chart updates are in the form of data to be written to specific fields in the patient chart (i.e., notes), as a rendered document including images, or both. In one embodiment, the patient and procedure information data is transmitted (Steps 702, 703) to the computer with an imaging device 110. The computer with an imaging device 110 is part of a data processing system 700 for tracking, confirming, and storing patient and procedure information using a unique device identifier 150 associated with a medical device 140. In this data processing system 700, an application 210, i.e. a software application, is used by a computer with an imaging device 110 having internet connectivity to validate a unique device identifier 150 across multiple servers.

An image of the unique device identifier 150 is taken and decoded by the computer with an imaging device 110. In one embodiment, the HIPAA-compliant application local server 193 interprets the data received related to the unique device identifier 150 associated with a medical device 140 by applying the computer program product 210. The unique device identifier 150 is verified and confirmed by comparison with the corresponding unique device identifier shown in the GUDID database 146, (that has been downloaded to the local HIPPA-compliant server 193), to provide the option to accept the unique device identifier by user 192. The HIPAA-compliant application local server 193 provides the output to either a web server and/or to the display portion 194 of the computer with an imaging device 110 for the User 192 to view while in the procedure or operating room. If the output is accepted the unique device identifier and the patient and procedure information are transmitted (Step 718) to a HIPAA-compliant application remote server 190. The data is also transmitted (Step 717) to EHR/EMR 141 to update the patient's chart and can be further used by a hospital database for inventory management.

Figure 8B:
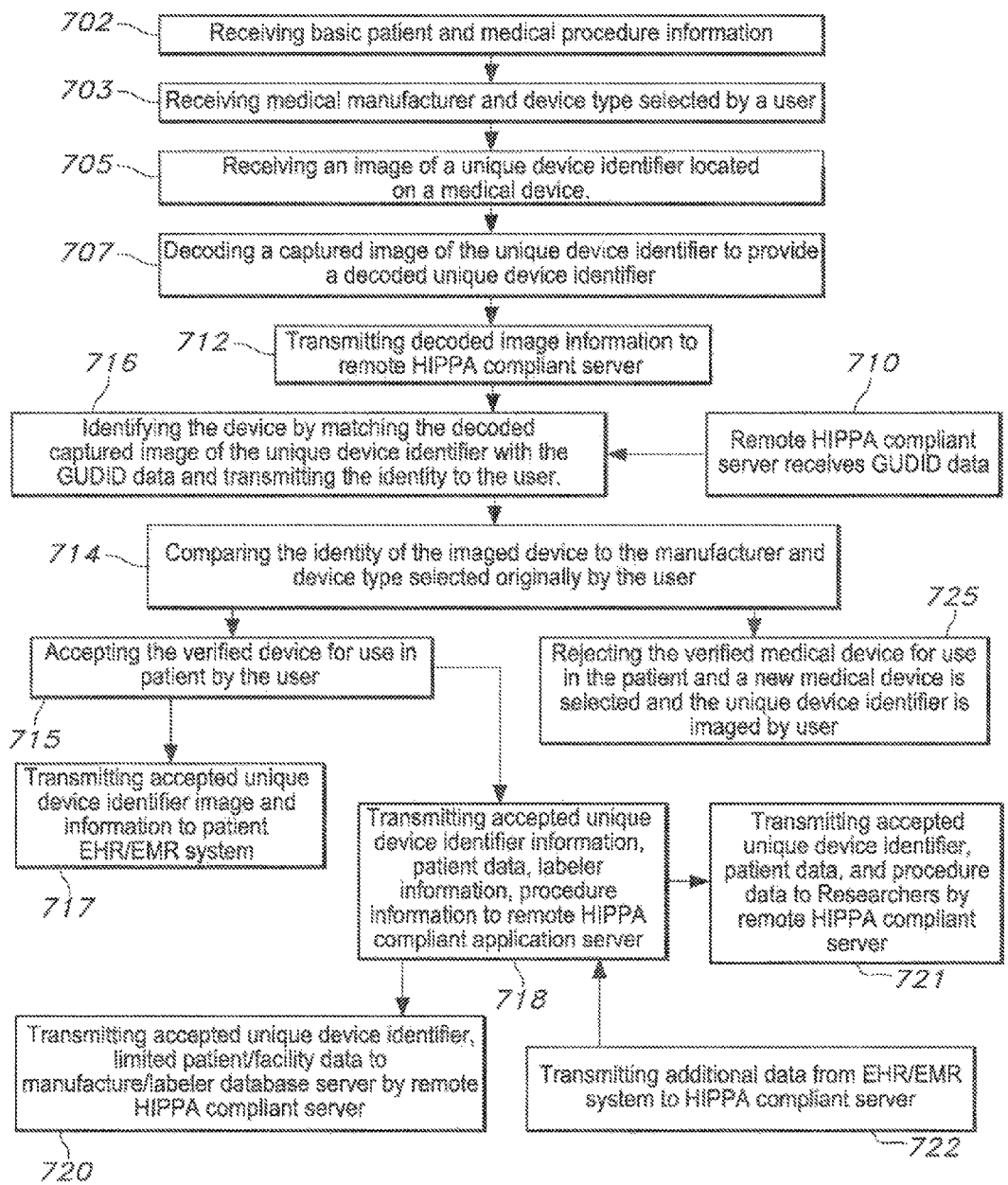
FIG. 8B shows an embodiment of the process steps of the present invention in the embodiment of GUDID data loaded on to a remote HIPPA-compliant server.

Now referring to FIGS. 8B and 9B, an alternative embodiment the GUDID data is loaded to a remote HIPPA-compliant server in system 700, the non-transitory computer-readable medium having embodied thereon an at least one application, the at least one application being executable by a processor, to perform a method, the method involving the steps of: receiving basic patient and medical procedure information (Step 702); receiving medical device manufacturer and device type selected by a user (Step 703); receiving an image of a unique device identifier located on a medical device present in a sterile setting, the image of a unique device identifier captured with a computer with an imaging device within the sterile field (Step 705); decoding a captured image of the unique device identifier to provide a decoded unique device identifier for the device in the sterile setting (Step 707); transmitting the decoded captured image of the unique device identifier to the remote HIPPA-compliant server (Step 712); the remote HIPPA-compliant server receives GUDID data (Step 710); identifying the medical device by matching the decoded captured image of the Unique Device Identifier affixed to the medical device with the Global Unique Device Identifier Database data at the remote HIPPA-compliant server and transmitting this identity to the user (Step 716); comparing the identity of the imaged device to the manufacturer and device type selected originally by the user to verify that the imaged device is correct for the patient (Step 714); requiring the user to accept (Step 715) or reject (Step 725) the medical device for use in the patient thereby receiving a designation that the user accepts the verified device for use in the patient (Step 715) or receiving a designation that the user rejects the verified device for use in a patient, and a new medical device is selected by the user (Step 725).

If the device is accepted by the user, the method can further include the steps of: transmitting the accepted unique device identifier information, patient data, labeler information and procedure information to the remote HIPPA compliant application server (Step 718). The method can further include the steps of: transmitting the accepted unique device identifier, patient data, and facility data to a manufacturer or a labeler database server from the remote HIPPA compliant server (Step 720). The method can further include the step of: transmitting the accepted unique device identifier, patient data, and facility data to a patient chart in an EHR/EMR system (Step 717). The information sent to the EMR/EHR includes the actual captured image of the medical device in addition to the UDI information. This is important so someone reviewing the medical record could identify the device without having to refer to a UDI database to visually identify the implanted device that corresponds with the UDI. In these embodiments, the EHR/EMR system transfers information to the remote HIPPA-compliant data base in (Step 722). The type of information flowing to the remote HIPPA-compliant database from the EMR in Step 722, could include comorbidities, prior surgeries or treatments, medication usage etc. The accepted UDI, patient data, and procedure data stored in the remote HIPPA-compliant server can be transmitted to Researchers (Step 721) in each embodiment.

In an exemplary embodiment, the transmission of decoded image along with the inputted patient/procedure data is sent to the remote server 190, which has the GUDID data on it and is where the comparison will occur. Various interface 114 protocols can be used for inputting patient and procedure information. In one embodiment, the computer with an imaging device 110 communicates directly with EHR/EMR 141 by using an API provided by the EHR/EMR 141, by HL7 messaging or by using SFTP or network folder to exchange files.

The compared information is then transmitted to the computer with an imaging device 110 where the user 192 can view it and either accept or reject it. Once accepted the data is then transmitted back to the remote server 190 to be housed in the data repository 145. In an alternative embodiment, the GUDID data is on the computer with an imaging device 110. Image capture, decoding and comparison all happen on computer with an imaging device 110 and the user 192 accepts the medical device 140. In this illustrative embodiment, the accepted data is transmitted to the remote server 190 to be stored in the repository 145.

In this exemplary embodiment, a GUDID database 146 is accessed to verify the unique device identifier 150 associated with a medical device 140. The GUDID does not contain complete UDI information, rather it contains DI (device identifier which is the device type, but not the individual unique device) information which is only part of the UDI and is more general. The data is saved to a data repository 145, and can be retrieved by any internet capable device by subscription users 148, such as insurance payers and researchers. The saved accepted device information and patient usage data within the HIPAA-compliant application remote server 190 and data repository 145 is transmitted to the manufacturers/labelers 147 to be saved in their internal database. The HIPAA-compliant application remote server 190 or the HIPAA-compliant local server 193 can interpret the data received related to the unique device identifier 150 associated with a medical device 140 by applying the computer program product 210, and providing an output via a web server and/or to the display portion 194 of computer with an imaging device 110 for the user 192 to view and accept or reject the medical device as correct for the patient and procedure previously inputted (Steps 702, 703) while in the procedure or operating room.

An image of unique device identifier 150 is obtained and digitized by the application 210. In this data processing system 700, an application 210, i.e. a software application, is used by a computer with an imaging device 110 having internet connectivity to validate a unique device identifier 150 across multiple servers. An image of the unique device identifier 150 is taken and decoded by the computer with an imaging device 110. The HIPAA-compliant application remote server 190 interprets the data received related to the unique device identifier 150 associated with a medical device 140 by applying the computer program product 210. The unique medical device is accepted or rejected by comparison with the corresponding known unique device identifier shown in the GUDID database 146 by the user 192, to provide an accepted unique device identifier.

In one embodiment, a cross-server communication protocol is provided for cross-server communication with a HIPAA-compliant application remote server 190 that is configured to receive the accepted unique device identifier and the patient and procedure information which is stored for future use in a data base repository 145. The accepted unique device identifier is transmitted to a manufacturer/labeler database 147 by a cross-server communication protocol.

Figure 10:
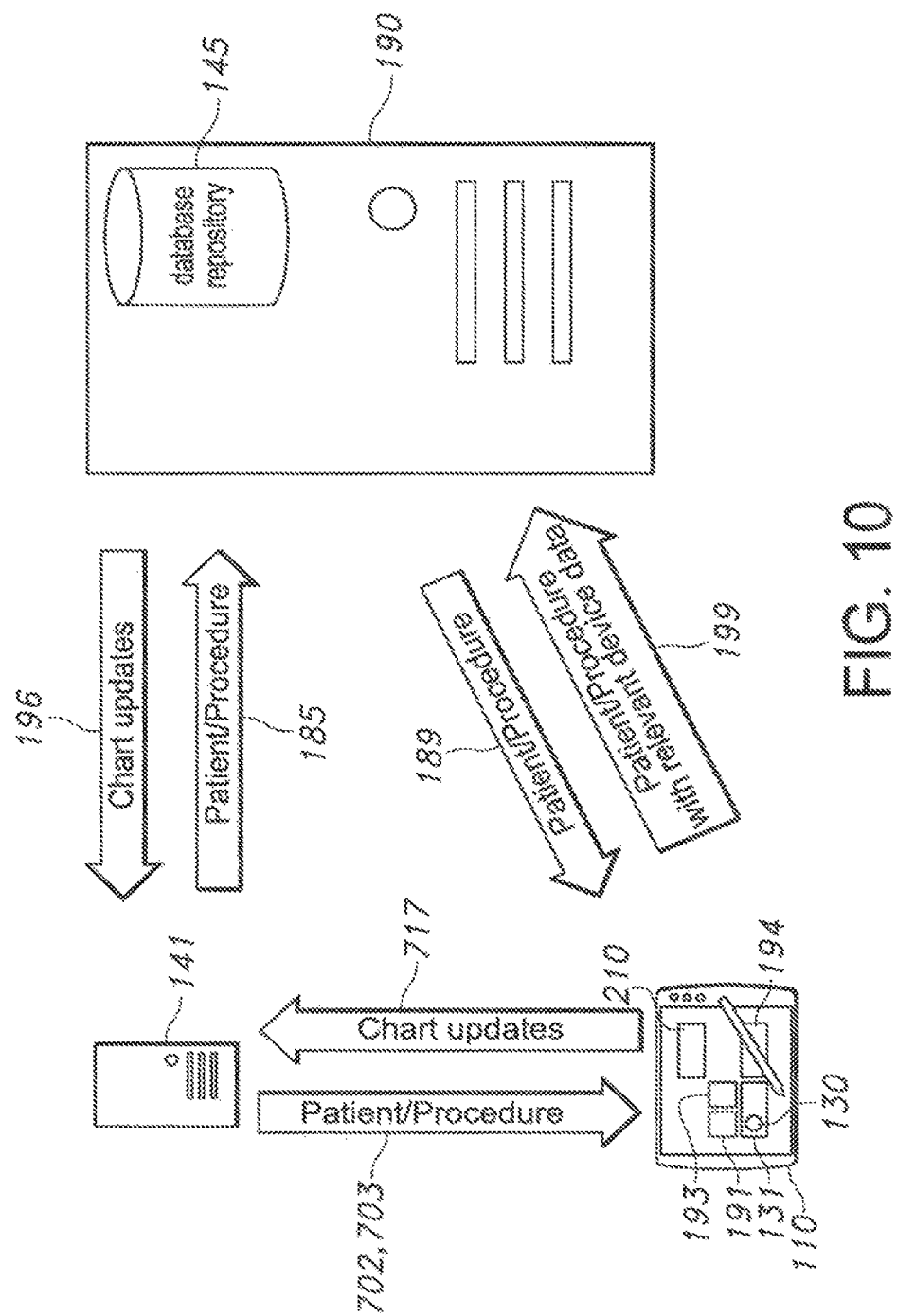
FIG. 10 shows an exemplary embodiment of an indirect connection wherein the data passes through the computer through a secure internet connection to the remote HIPAA-compliant application remote server.

In another embodiment, as shown in FIG. 10, an indirect connection is shown wherein the data passes through the computer through a secure internet connection to the HIPAA-compliant application remote server 190, where it is stored in the data base repository 145, before it is transmitted from the HIPAA-compliant application remote server 190 to the EHR/EMR 141. In an alternative embodiment, the private network hosting the EHR/EMR 141 is accessed by a HIPAA-compliant application remote server 190 or a client application (not shown) is installed on the EHR/EMR 141. This allows the EHR/EMR 141 to make an outbound connection. Chart updates occur depending on the type of EHR/EMR 141 system, chart updates are in the form of data to be written to specific fields in the patient chart (i.e., notes), as a rendered document including images or both. The patient and procedure information data is transmitted to the HIPAA-compliant application remote server 190. The patient and procedure information data is transmitted 189 to the computer with an imaging device 110 which includes a database 191, a server 193 and a computer program product 210 configured to acquire information related to the unique device identifier 150. Similarly, the patient and procedure information and relevant device data is transmitted 199 to the HIPAA-compliant remote server 190. The accepted unique device identifier data is also sent to the HIPAA-compliant application remote server 190 and saved within data base repository 145 for data retrieval, such as by a hospital for inventory management. The computer with an imaging device 110 can be linked directly to the EHR/EMR 141 or connected through the HIPAA-compliant application remote server 190. An image of the unique device identifier 150 is obtained and digitized by the processor executing a computer program product 210.

Equivalent elements can be substituted for the ones set forth above such that they perform in substantially the same manner in substantially the same way for achieving substantially the same result. It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages.

The invention claimed is:

1. A flexible sterile enclosure for receiving and isolating a non-sterile computer apparatus, wherein the flexible sterile enclosure s comprised of:
   a container portion having a top and a bottom surface, wherein the container portion has a plurality of closed edges and an open section configured to receive the non-sterile computer with an imaging device, wherein the bottom surface of the container portion has an optical aperture positioned to coordinate with the lens of a camera of non-sterile computer with an imaging device;
   a folded back flap portion on the bottom surface, said folded back flap portion having two short closed aide ends and a top edge and a bottom edge, said bottom edge forming an opening configured to allow the flexible sterile enclosure to contact a front surface of a frame, a portion of a bottom surface of the frame and a plurality of front aide end surfaces of the frame; and
   a closure means for sealing the flexible sterile enclosure.

2. The flexible sterile enclosure of claim 1 wherein the closure means is comprised of a flap portion made of the plurality of side flaps and the central flap.

3. The flexible sterile enclosure of claim 1 wherein the optical aperture is surrounded by a gasket.

4. A method to position a non-sterile computer apparatus within a flexible sterile enclosure to obtain an image of a unique device identifier on the medical device wherein the sterile enclosure is comprised of:
   a container portion having a top and a bottom surface, wherein the container portion has a plurality of closed edges and an open section configured to receive the computer with an imaging device, wherein the bottom surface of the container portion has an optical aperture positioned to coordinate with a lens of a camera; a folded back flap portion, a central flap and a plurality of side flaps, wherein the plurality of side flaps and the central flap have an adhesive to facilitate the sealing of the sterile enclosure;
   inserting the sterile enclosure on to a top surface of a frame; wherein the sterile enclosure has an optical aperture surrounded by a gasket;
   positioning the optical aperture of the sterile enclosure through a frame aperture in a base of the frame to concentrically locate the gasket and the optical aperture with the frame aperture;
   positioning the folded back flap portion of the sterile enclosure to contact a front surface of the frame and a portion of a bottom surface of the frame and a plurality of front side end surfaces of the frame;
   positioning the computer with an imaging device within the sterile enclosure to associate the lens of the computer with an imaging device with the optical aperture of sterile enclosure;
   enclosing the computer with an imaging device within the sterile enclosure by sealing the front flap to the bottom surface of the frame and the plurality of side flaps around a sealed central flap, the top of the sterile enclosure; and
   passing a medical device with a unique device identifier under the frame to obtain an image of the unique device identifier.

* * * * *